United States Patent [19]

Taneja et al.

[11] Patent Number: 6,000,061
[45] Date of Patent: Dec. 14, 1999

[54] GLOVE MADE FROM A BLEND OF CHLOROPRENE RUBBER AND A CARBOXYLATED SYNTHETIC BUTADIENE RUBBER

[75] Inventors: Anil Taneja, New Delhi; Karunanithy Chandra Sekaran, Chennai, both of India

[73] Assignee: PT. Irama Dinamika Latex, Medan, Indonesia

[21] Appl. No.: 09/195,247

[22] Filed: Nov. 18, 1998

[51] Int. Cl.$^6$ ...................................................... A41D 19/00
[52] U.S. Cl. .................................................. 2/168; 2/161.7
[58] Field of Search ......................... 2/159, 161.7, 161.8, 2/167, 168

[56] References Cited

U.S. PATENT DOCUMENTS

| | | | |
|---|---|---|---|
| Re. 35,616 | 9/1997 | Tillotson et al. | 2/168 |
| 3,411,982 | 11/1968 | Kavalir et al. | |
| 4,218,779 | 8/1980 | Hart et al. | |
| 4,748,051 | 5/1988 | Songer et al. | 427/212 |
| 5,014,362 | 5/1991 | Tillotson et al. | |
| 5,039,750 | 8/1991 | Miller et al. | |
| 5,070,540 | 12/1991 | Bettcher et al. | 2/2.5 |
| 5,195,537 | 3/1993 | Tillotson . | |
| 5,459,880 | 10/1995 | Sakaki et al. | 2/168 |
| 5,540,963 | 7/1996 | Wong | 428/35.7 |
| 5,570,475 | 11/1996 | Nile et al. | |
| 5,571,219 | 11/1996 | Gorton . | |
| 5,670,263 | 9/1997 | Gazeley | 428/492 |

*Primary Examiner*—Diana Oleksa
*Assistant Examiner*—Katherine Moran
*Attorney, Agent, or Firm*—Finnegan, Henderson, Farabow, Garrett & Dunner, L.L.P.

[57] ABSTRACT

A glove comprising an elastomeric blend of chloroprene rubber and a carboxylated synthetic butadiene rubber. A preferred glove of the invention is a medical glove comprising an elastomeric blend of chloroprene rubber and one of carboxylated nitrile butadiene rubber or carboxylated styrene butadiene rubber. The glove not only reduces the risk associated with natural rubber gloves of causing allergenic reaction and shock to the wearer, but also better approximates the feel and stretch of natural rubber gloves than do other elastomeric gloves.

23 Claims, No Drawings

GLOVE MADE FROM A BLEND OF CHLOROPRENE RUBBER AND A CARBOXYLATED SYNTHETIC BUTADIENE RUBBER

BACKGROUND OF THE INVENTION

1. Field of the Invention

The present invention relates to a glove, and more particularly to a glove comprising an elastomeric blend of chloroprene rubber and a carboxylated synthetic butadiene rubber. A preferred glove of the invention is a medical glove comprising an elastomeric blend of chloroprene rubber and one of carboxylated nitrile butadiene rubber or carboxylated styrene butadiene rubber.

2. Description of the Related Art

Individuals working in hospitals, nursing homes, and other health care facilities regularly wear medical gloves to protect themselves from possible infection or to otherwise prevent their hands from contacting harmful substances. Fear of infection, particularly driven by the advent of the human immunodeficiency virus ("HIV") in the 1980s, has especially contributed to the increased use of medical gloves by health care professionals.

Conventional medical gloves are typically made from natural rubber latex, a latex derived from the sap of the Hevea Brasiliensis tree. Medical gloves made from natural rubber possess a number of favorable qualities. For instance, natural rubber gloves have a high intrinsic elasticity and therefore provide the wearer with considerable sensitivity to the touch for gripping or handling items. Natural rubber film also offers substantial protection to the wearer as an effective barrier from pathogens, virus, and bacteria. Finally, natural rubber is inexpensive and is available in large quantities.

Some users of natural rubber medical gloves experience allergenic reactions, and even anaphylactic shock, upon contact with the gloves. These individuals typically wear the gloves frequently throughout their careers and are therefore in contact with the gloves for substantial combined periods of time. The apparent cause of the reactions and shock is the presence of proteins inherent in natural rubber. Some members of the health care industry have therefore sought synthetic alternatives to natural rubber gloves to alleviate the risk of reactions and shock to the wearer.

The search for a suitable and effective substitute for natural rubber in medical gloves has been difficult. Conventional materials such as vinyl, nitrile, and styrene butadiene rubber have been used as substitutes for natural rubber, yet these materials typically suffer from a number of disadvantages. Gloves made from any of those materials usually lack the distinctive feel and stretch of natural rubber gloves, thereby often failing to provide the sensitivity to touch required by the wearer. Furthermore, vinyl rubber is solvent-based and therefore tends to be more difficult to produce and more hazardous to handle and use than natural rubber. Lastly, vinyl and nitrile are typically both tough, and they may tear easily and stretch poorly. There is, therefore, a need in the health care industry for an elastomeric glove that not only reduces the risk of allergenic reaction and shock to the wearer, but also better approximates the feel and stretch of natural rubber gloves than do other elastomeric gloves.

BRIEF SUMMARY OF THE INVENTION

An object of the present invention is to provide a glove that reduces the risk associated with natural rubber gloves of causing allergenic reactions and anaphylactic shock to the wearer. Another object of the invention is to provide a glove that better approximates the desirable feel and stretch of natural rubber gloves than do other elastomeric gloves.

The present invention fulfills these objects by providing a glove comprising an elastomeric blend of chloroprene rubber and a carboxylated synthetic butadiene rubber. A preferred glove of the invention is a medical glove comprising an elastomeric blend of chloroprene rubber and one of carboxylated nitrile butadiene rubber or carboxylated styrene butadiene rubber. Additional features and advantages of the invention are set forth in the description that follows, and in part will be apparent from the description or may be learned from practice of the invention. The advantages of the invention will be realized and attained by the gloves particularly pointed out in the written description and claims.

Both the foregoing general description and the following detailed description of the invention are exemplary and explanatory only and are not restrictive of the claimed invention.

DETAILED DESCRIPTION OF THE INVENTION

The chloroprene rubber, carboxylated nitrile butadiene rubber, carboxylated styrene butadiene rubber, and other carboxylated synthetic butadiene rubbers referred to in the present invention are generally known by those skilled in the art and are readily obtainable from a number of sources in the United States and abroad. The gloves of the present invention may contain from about 50% to about 80% of chloroprene rubber by weight of the rubber blend. A glove made from a blend of chloroprene rubber and carboxylated nitrile butadiene rubber preferably contains a blend containing about 60% to about 70% of chloroprene rubber, and more preferably about 60% chloroprene rubber.

The gloves of the present invention may contain an effective amount of an additive suitable for use in gloves. Suitable additives include zinc dibutyldithiocarbamate, zinc oxide, sulphur, Vulcanox BKF, titanium dioxide and potassium laurate or ammonium laurate. The additives may be present in the gloves in suitable proportions by weight of the rubber blend. Zinc dibutyldithiocarbamate is an accelerating agent, sulphur is added to complete the curing and crosslinking of the rubber, titanium dioxide is present as a pigment, and potassium laurate or ammonium laurate is used to stabilize the glove composition. Zinc oxide promotes and enhances crosslinking and cure of the rubber and functions as an acid acceptor to improve the rubber's resistance to heat, light, and aging. Lastly, Vulcanox BKF is an antioxidant and prevents deterioration of the rubber's color during processing and aging and helps the rubber attain optimum tensile properties.

Preferably, the gloves contain the additives shown in Table 1 in the indicated proportions by weight of the rubber blend:

TABLE 1

| Additive | Proportion of Additive in Parts per Hundred by Weight of the Rubber Blend (PHR) |
| --- | --- |
| Zinc dibutyldithiocarbamate | 0.4 to 1 |
| Zinc oxide | 4.5 to 5 |
| Sulphur | 0.5 to 0.8 |
| Vulcanox BKF | 1 to 2 |
| Titanium dioxide | 1 |

TABLE 1-continued

| Additive | Proportion of Additive in Parts per Hundred by Weight of the Rubber Blend (PHR) |
|---|---|
| Potassium laurate or Ammonium laurate | 0.1 |

Gloves made from a blend of chloroprene rubber and carboxylated nitrile butadiene rubber more preferably contain 0.85 PHR zinc dibutyldithiocarbamate, 4.5 PHR zinc oxide, 0.5 PHR sulphur, 1.0 PHR Vulcanox BKF, 1.0 PHR titanium dioxide, and 0.1 PHR potassium laurate or ammonium laurate.

The gloves of the present invention better approximate the desirable feel and stretch of natural rubber gloves than do other elastomeric gloves. In particular, the gloves of the present invention made from a blend of chloroprene rubber and carboxylated nitrile butadiene rubber may have the following properties: a tensile strength of from about 11 MPa to about 15 MPa, preferably about 15 MPa; an elongation at break from about 600% to about 720%, preferably about 720%; a modulus at 300% from about 1.8 MPa to about 2.5 MPa, preferably about 1.8 MPa; and a modulus at 500% from about 3.9 MPa to about 4.4 MPa, preferably about 3.9 MPa.

Gloves of the present invention made from a blend of chloroprene rubber and carboxylated styrene butadiene rubber may have a tensile strength of about 20 MPa, a modulus at 300% of about 4.5 MPa, and a modulus at 500% of about 8.0 MPa.

Tensile strength, elongation at break, and modulus properties are well known in the art. Tensile strength is the energy required to stretch the glove material to the breaking point. Elongation at break is the percent stretch of the glove material at the breaking point. The 300% and 500% modulus is the energy required to stretch the glove material 300% or 500% of a predetermined length, respectively.

Medical gloves and methods of making medical gloves are generally well known in the art. The term "medical glove" used herein refers to elastomeric hand protection used in the health care industry and scientific community. Such hand protection includes gloves commonly known as examination gloves, surgeon's gloves, procedure gloves, and dental care gloves. U.S. Pat. No. 5,014,362, incorporated in its entirety by reference herein, describes in detail a commonly used method of making medical gloves.

In preparing the gloves of the present invention, a latex blend of rubber, e.g., chloroprene rubber and carboxylated nitrile butadiene rubber, is mixed with one or more additives, e.g., zinc dibutyldithiocarbamate, zinc oxide, sulphur, Vulcanox BKF, titanium dioxide, and/or potassium or ammonium laurate. The mixture is then set aside to mature for several hours.

Glove formers are cleaned, e.g., by washing with a detergent such as trisodium phosphate and a mild acid solution such as a nitric acid solution, and then rinsed with warm water. The cleaned formers are dried and then dipped into a coagulant mixture of calcium nitrate, a non-anionic wetting agent such as a fatty alcohol ethoxylate solution, a mold release agent such as calcium carbonate or a mixture of stearic acid and wax, and water. The coagulant on the formers is then dried with application of heat. The formers covered with dried coagulant are then dipped into the desired latex mixture and then withdrawn and the latex coating is allowed to gel and is then leached in water.

When powder-free gloves are desired, the coated formers are dipped into a powder-free polymer-based solution for coating with a donning aid. One such solution is a polyurethane and silicone solution. The coated formers are then placed in an oven to cure at a temperature ranging from 90° C. to 140° C. The formers are thereafter dipped in warm water for post-cure leaching. The latex on the formers is then dried, cooled, and stripped from the formers.

When powdered gloves are desired, the coated formers are placed in an oven to cure the latex at a temperature ranging from 90° C. to 140° C. The formers are then dipped in warm water for post-cure leaching and subsequently dipped in a powder slurry made, for example, of corn starch powder. The slurry is then dried and the latex is stripped from the formers.

The present invention is further illustrated by the following examples which are designed to teach those of ordinary skill in the art how to practice the invention. The following examples are merely illustrative of the invention and should not be construed as limiting the invention as claimed.

Examples 1–4 illustrate various beneficial physical properties of certain preferred gloves of the present invention.

EXAMPLES 1–4

Four different medical gloves were made from a latex blend of chloroprene rubber and carboxylated nitrile butadiene rubber. The gloves were made to contain ratios of chloroprene rubber to carboxylated nitrile butadiene rubber as shown in Table 2. Each blend was then mixed with 0.85 PHR zinc dibutyldithiocarbamate, 4.5 PHR zinc oxide, 0.5 PHR sulphur, 1.0 PHR Vulcanox BKF, 1.0 PHR titanium dioxide, and 0.1 PHR ammonium laurate. The mixtures were then set aside to mature for several hours.

Glove formers were cleaned by washing with a detergent of trisodium phosphate and a mild nitric acid solution, and then rinsed with warm water. The cleaned formers were dried and then dipped into a coagulant mixture of calcium nitrate, the non-anionic wetting agent Terric 320, the mold release agent of stearic acid and wax, and water. The coagulant mixture on the formers was then dried with application of heat. The formers covered with dried coagulant mixture were then dipped into the desired latex mixture and then withdrawn and the latex coating was allowed to gel and was then leached in water. The coated formers were placed in an oven to cure the latex at a temperature escalating in order from 95° C., to 105° C., to 115° C., and finally to a temperature of 120° C. Each latex was then stripped from the formers.

The tensile strength, modulus at 300%, modulus at 500%, and elongation at break were measured for each glove and the measured data is presented in Table 2.

TABLE 2

| Example | Ratio of chloroprene rubber to carboxylated nitrile butadiene rubber | Tensile Strength (MPa) | Modulus at 300% (MPa) | Modulus at 500% (MPa) | Elongation at Break (%) |
|---|---|---|---|---|---|
| 1 | 50:50 | 12.45 | 2.5 | 4.4 | 620 |
| 2 | 60:40 | 14.49 | 1.95 | 4.0 | 720 |
| 3 | 70:30 | 15.15 | 1.8 | 4.0 | 720 |
| 4 | 80:20 | 11.37 | 1.85 | 3.9 | 600 |

Example 5 compares the physical properties of a preferred glove of the present invention with those of natural rubber gloves and nitrile gloves.

EXAMPLE 5

Medical gloves containing a blend of 60% chloroprene rubber and 40% carboxylated nitrile butadiene rubber were made following the procedure of Example 2. The tensile strength, modulus at 300%, modulus at 500%, and elongation at break of the gloves were compared with the same physical properties of natural rubber gloves and nitrile gloves. The data presented in Table 3 summarizes these measurements.

TABLE 3

| Type of Glove | Tensile Strength (MPa) | Modulus at 300% (MPa) | Modulus at 500% (MPa) | Elongation at Break (%) |
|---|---|---|---|---|
| 60:40 blend chloroprene rubber and carboxylated nitrile butadiene rubber | 14.49 | 1.95 | 4.0 | 720 |
| Natural rubber gloves | 24 | 1.75 | 2.0 | 750 |
| Nitrile gloves | 12 | 2.1 | 4.3 | 700 |

Example 6 illustrates various beneficial physical properties of certain preferred gloves of the invention.

EXAMPLE 6

A medical glove made from a latex blend of 70% chloroprene rubber and 30% carboxylated styrene butadiene rubber was made following the general procedure described in Examples 1–4. The glove was made to contain 5 PHR zinc oxide, 1 PHR Vulcanox BKF, 0.8 PHR sulfur, 0.9 PHR zinc dibutyldithiocarbamate, 1.0 PHR titanium dioxide, and 0.1 PHR ammonium laurate.

The tensile strength, modulus at 300%, and modulus at 500% were measured for the glove and the measured data is presented in Table 4.

TABLE 4

| Type of Glove | Tensile Strength (MPa) | Modulus at 300% (MPa) | Modulus at 500% (MPa) |
|---|---|---|---|
| 70:30 blend chloroprene rubber and carboxylated styrene butadiene rubber | 20 | 4.5 | 8.0 |

The foregoing written description relates to various embodiments of the present invention. Numerous changes and modifications may be made therein without departing from the spirit and scope of the invention as defined in the following claims.

What is claimed is:

1. A glove comprising an elastomeric blend of chloroprene rubber and a carboxylated synthetic butadiene rubber.

2. A glove as claimed in claim 1, comprising an elastomeric blend of chloroprene rubber and carboxylated nitrile butadiene rubber.

3. A glove as claimed in claim 2, wherein the blend contains from about 50% to about 80% of chloroprene rubber by weight of the blend.

4. A glove as claimed in claim 2, wherein the blend contains from about 60% to about 70% of chloroprene rubber by weight of the blend.

5. A glove as claimed in claim 2, wherein the blend contains about 60% of chloroprene rubber by weight of the blend.

6. A glove as claimed in claim 2, wherein the blend also contains effective amounts of zinc dibutyldithiocarbamate, zinc oxide, sulphur, Vulcanox BKF, titanium dioxide, and potassium laurate or ammonium laurate.

7. A glove as claimed in claim 6, wherein the zinc dibutyldithiocarbamate is present in an amount of about 0.4 to 1 part, the zinc oxide is present in an amount of about 4.5 to 5 parts, the sulphur is present in an amount of about 0.5 to 0.75 part, the Vulcanox BKF is present in an amount of about 1 to 2 parts, the titanium dioxide is present in an amount of about 1.0 part, and the potassium laurate or ammonium laurate is present in an amount of about 0.1 part, each part per hundred parts by weight of the blend.

8. A glove as claimed in claim 7, wherein the zinc dibutyldithiocarbamate is present in an amount of about 0.85 part, the zinc oxide is present in an amount of about 4.5 parts, the sulphur is present in an amount of about 0.5 part, the Vulcanox BKF is present in an amount of about 1.0 part, the titanium dioxide is present in an amount of about 1.0 part, and the potassium laurate or ammonium laurate is present in an amount of about 0.1 part, each part per hundred parts by weight of the blend.

9. A glove as claimed in claim 2, having a tensile strength of from about 11 MPa to about 15 MPa, an elongation at break of from about 600% to about 720%, a modulus at 300% of from about 1.8 MPa to about 2.5 MPa, and a modulus at 500% of from about 3.9 MPa to about 4.4 MPa.

10. A glove as claimed in claim 9, wherein the glove has a tensile strength of about 15 MPa, an elongation at break of about 720%, a modulus at 300% of about 1.8 MPA, and a modulus at 500% of about 3.9 MPa.

11. A glove as claimed in claim 2, wherein the glove is a medical glove.

12. A medical glove as claimed in claim 11, wherein the blend contains about 60% of chloroprene rubber by weight of the blend.

13. A medical glove as claimed in claim 11, wherein the blend also contains effective amounts of zinc dibutyldithiocarbamate, zinc oxide, sulphur, Vulcanox BKF, titanium dioxide, and potassium laurate or ammonium laurate.

14. A medical glove as claimed in claim 11, wherein the glove has a tensile strength of from about 11 MPa to about 15 MPa, an elongation at break of from about 600% to about 720%, a modulus at 300% of from about 1.8 MPa to about 2.5 MPa, and a modulus at 500% of from about 3.9 MPa to about 4.4 MPa.

15. A glove as claimed in claim 1, comprising an elastomeric blend of chloroprene rubber and carboxylated styrene butadiene rubber.

16. A glove as claimed in claim 15, wherein the blend contains from about 50% to about 80% of chloroprene by weight of the blend.

17. A glove as claimed in claim 15, wherein the blend contains about 70% of chloroprene by weight of the blend.

18. A glove as claimed in claim 15, wherein the blend also contains effective amounts of zinc dibutyldithiocarbamate, zinc oxide, sulphur, Vulcanox BKF, titanium dioxide, and potassium laurate or ammonium laurate.

19. A glove as claimed in claim 15, having a tensile strength of about 20 MPa, a modulus at 300% of about 4.5 MPa, and a modulus at 500% of about 8.0 MPa.

20. A glove as claimed in claim 15, wherein the glove is a medical a glove.

21. A medical glove as claimed in claim 20, wherein the blend contains from about 50% to about 80% of chloroprene by weight of the blend.

22. A medical glove as claimed in claim 20, wherein the blend also contains effective amounts of zinc dibutyldithiocarbamate, zinc oxide, sulphur, Vulcanox BKF, titanium dioxide, and potassium laurate or ammonium laurate.

23. A medical glove as claimed in claim 20, having a tensile strength of about 20 MPa, a modulus at 300% of about 4.5 MPa, and a modulus at 500% of about 8.0 MPa.

* * * * *